United States Patent [19]
Kawabe et al.

[11] Patent Number: 5,618,804
[45] Date of Patent: Apr. 8, 1997

[54] METHANEDIPHOSPHONIC ACID DERIVATIVE, PROCESS FOR PRODUCTION THEREOF AND USE FOR PHARMACEUTICALS

[75] Inventors: Norio Kawabe, Fujisawa; Hiromi Uchiro, Kamakura; Teruo Nakadate, Yokohama; Masahiko Tanahashi, Kamakura; Yuriko Funaba, Fujisawa, all of Japan

[73] Assignee: Toray Industries, Inc., Tokyo, Japan

[21] Appl. No.: 178,320

[22] PCT Filed: Jan. 8, 1993

[86] PCT No.: PCT/JP93/00014

§ 371 Date: Jan. 14, 1994

§ 102(e) Date: Jan. 14, 1994

[87] PCT Pub. No.: WO94/01442

PCT Pub. Date: Jan. 20, 1994

[30] Foreign Application Priority Data

Jul. 10, 1992 [JP] Japan ................ 4-183866

[51] Int. Cl.[6] .............. A61K 31/66; C07F 9/38; C07F 9/40
[52] U.S. Cl. .............. 514/103; 514/105; 558/161; 562/21
[58] Field of Search .............. 558/161; 562/21; 514/103, 105

[56] References Cited

U.S. PATENT DOCUMENTS

| | | |
|---|---|---|
| 3,683,080 | 8/1972 | Francis . |
| 4,020,091 | 4/1977 | Budnick . |
| 4,473,560 | 9/1984 | Biere et al. . |
| 4,503,049 | 3/1985 | Biere et al. . |
| 4,503,094 | 3/1985 | Breuninger et al. . |
| 4,732,998 | 3/1988 | Binderup ................ 558/161 |
| 4,746,654 | 5/1988 | Breliere et al. ................ 514/108 |
| 4,876,247 | 10/1989 | Barbier et al. ................ 514/89 |
| 4,876,248 | 10/1989 | Breliere et al. ................ 514/108 |
| 4,902,679 | 2/1990 | Benedict et al. ................ 514/86 |
| 5,043,330 | 8/1991 | Nguyen et al. ................ 514/107 |
| 5,128,331 | 7/1992 | Nguyen et al. ................ 514/101 |
| 5,153,183 | 10/1992 | Kawabe et al. ................ 514/76 |

FOREIGN PATENT DOCUMENTS

| | | |
|---|---|---|
| 2025268 | 3/1991 | Canada . |
| 0084822 | 8/1983 | European Pat. Off. . |
| 0085321 | 8/1983 | European Pat. Off. . |
| 0418064 | 3/1991 | European Pat. Off. . |
| 0440809 | 8/1991 | European Pat. Off. . |
| 58-174393 | 10/1983 | Japan . |
| 58-174394 | 10/1983 | Japan . |
| 61-503034 | 12/1986 | Japan . |
| 63-185993 | 8/1988 | Japan . |
| 3112994 | 5/1991 | Japan . |
| WO8600902 | 2/1986 | WIPO . |

OTHER PUBLICATIONS

Journal of Medicinal Chemistry, vol. 30, No. 8, 1987 Washington, US pp. 1426–1433.
Chemical Abstracts, vol. 109, No. 224084; Krainev, A.G. et al. Biol. Membr. 1988, 5(8), 795–806.
Chemical Abstracts, vol. 108, No. 186839; Alfer'ev, I.S. et al. Izv. Akad. Nauk SSSR, Ser. Khim. 1987, (4), 860–864.

Primary Examiner—Johann Richter
Assistant Examiner—Michael Ambrose
Attorney, Agent, or Firm—Birch, Stewart, Kolasch & Birch

[57] ABSTRACT

A methane diphosphonic acid derivative represented by the general formula (I):

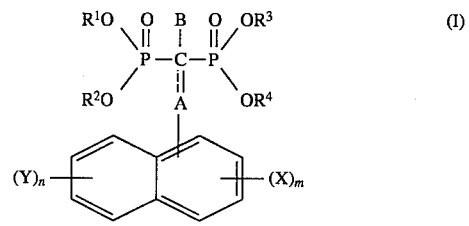

wherein, X and Y are defined in the specification; m represents an integer of 0 to 3; n represents an integer of 0 to 4; and each X of the $(X)_m$ and each Y of the $(Y)_n$ may be either identical or different; ... represents a double bond or single bond; A is $-(CH_2)a-(D)b-(CH_2)c-$ (wherein D is sulfur, oxygen, NH, alkyl-substituted N, or $CH_2$, a and c are integers of 0 to 10 and b is 0 or 1), or $-(CH=CH)d=CH=$ (wherein d is an integer of 0 to 2, and B does not exist when A represents $-CH=CH)d-CH=$), B refers to a hydrogen atom, alkyl group, amino group, monoalkylamino group, dialkylamino group, acylamino group, hydroxyl group, alkoxy group, trialkylsiloxy group or acyloxy group, and each of $R^1$, $R^2$, $R^3$ and $R^4$ is hydrogen atom, straight or branched alkyl group having 1 to 7 carbon atoms, or pharmacologically allowed cation, and these may be identical or different, as described. The compounds of the present invention have excellent IL-1 inhibitory action, antioxidative action and bone resorption inhibitory action, and are useful as an antiinflammatory drug, antirheumatic drug, or autoimmune disease drug.

13 Claims, No Drawings

METHANEDIPHOSPHONIC ACID DERIVATIVE, PROCESS FOR PRODUCTION THEREOF AND USE FOR PHARMACEUTICALS

TECHNICAL FIELD

The present invention relates to a novel methanediphosphonic acid derivative which inhibits actions of interleukin-1 that mediates pyrexia-inducing reactions, inflammation-inducing reactions, activates various blood cells and has bone destructive action, while simultaneously having an action to inhibit active oxygen that cause cell damage and fat denaturation, as well as an action to inhibit bone destruction during osteoporosis and chronic articular rheumatism.

BACKGROUND ART

Many of the diphosphonic acid compounds that have been developed mainly as drugs for treatment of bone metabolic diseases thus far have an action to inhibit bone destruction, and have been expected to inhibit bone destruction during the occurrence of arthritis such as chronic articular rheumatism. Although compounds having a diphosphonic acid structure are disclosed in Japanese Unexamined Patent Publication (Kokai) No. 59-42395, Japanese Unexamined Patent Publication (Kokai) No. 2-22285, Japanese Unexamined Patent Publication (Kokai) No. 3-77894 and Japanese Unexamined Patent Publication (Kokai) No. 60-174792, these diphosphonic acid compounds are primarily focused on inhibition of bone resorption. Although these compounds are effective as therapeutic drugs for bone metabolic disorders, they are still not adequate for treatment of chronic articular rheumatism.

In order for diphosphonic acid compounds to be used in the treatment of chronic articular rheumatism and so forth, a new drug is desired that, in addition to having an action to inhibit bone resorption, also has other, more effective actions, including inhibition of Interleukin-1 (abbreviated as IL-1), which is a mediator of inflammations, as well as inhibition of cell damage caused by activated neutrophils and macrophages.

IL-1 is known to be a mediator involved in pyrexia and inflammation, and its inhibitory agent is expected to be useful as an antiinflammatory drug. However, similar to many other cytokines, IL-1 is considered to mainly act locally. Although numerous substances have been reported to inhibit IL-1 in vitro, antiinflammatory drugs having action that allows adequate improvement of the disease state by actually inhibiting IL-1 in vivo have not yet been developed. In addition, invasion of activated neutrophils and macrophages at the site of inflammation have been observed during inflammations. Although the active oxygen produced by these blood cells has an action of heterogenous digestion, in cases where an inflammation has become chronic, these cells are known to damage normal tissue as well. Thus, compounds having both an IL-1 inhibiting action and antioxidative action are considered to be useful as not only antiinflammatory drugs, but also against autoimmune diseases such as chronic articular rheumatism, as well as organ disorders, such as those in the brain and liver, which occur during ischemia.

DISCLOSURE OF THE INVENTION

The present inventors conducted research on diphosphonic acid compounds that demonstrate excellent anti-inflammatory action, by giving to a diphosphonic acid derivatives not only action as therapeutic drugs for treatment of bone metabolic diseases, but also IL-1 inhibitory action and antioxidative action. During the course of this research, it was found that, if a naphthalene skeleton is given to a phosphonic acid structure, IL-1 inhibitory action and antioxidative action are provided that are not found in existing drugs.

The object of the present invention is to provide a useful, novel compound having an action to inhibit Interleukin-1, antioxidative action, and an action to inhibit bone destruction.

Namely, the present invention relates to the methane diphosphonic acid derivatives shown in general formula (I):

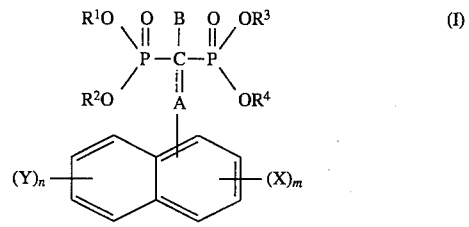

[wherein, X and Y represent substituent groups on the naphthyl group, and represent a halogen atom, nitro group, nitrile group, alkyl group, alkoxy group, trifluoromethyl group, the group:

(wherein $Z^1$ and $Z^2$ represent independently hydrogen atom or alkyl group, or $Z^1$ and $Z^2$ together may form a ring composed of carbon atoms or a ring composed of carbon atoms and hetero atom), the group:

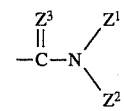

(wherein $Z^1$ and $Z^2$ are the same as above, and $Z^3$ represents oxygen or sulfur), thiol group, hydroxyl group, alkylthio group, arylthio group, acyloxy group, acylamino group, acylthio group, acyl group, alkenyl group, aryl group, cycloalkyl group, COOH group or COO-alkyl group; m represents an integer of 0 to 3, n represents an integer of 0 to 4, and each X of the $(X)_m$ and each Y of the $(Y)_n$ may be either identical or different; ⎓ represents a double bond or single bond; A is —(CH$_2$)a—(D)b—(CH$_2$)c— (wherein D is sulfur, oxygen, NH, alkyl-substituted N, or CH$_2$, a and c are integers of 0 to 10 and b is 0 or 1), or —(CH=CH)d—CH= (wherein d is an integer of 0 to 2, and B does not exist when A represents —CH=CH)d—CH=); B represents a hydrogen atom, alkyl group, amino group, monoalkylamino group, dialkylamino group, acylamino group, hydroxyl group, alkoxy group, trialkylsiloxy group or acyloxy group; and $R^1$, $R^2$, $R^3$ and $R^4$ are hydrogen atom, straight or branched chain alkyl group having 1 to 7 carbon atoms, or pharmacologically acceptable cation, and may be identical or different], a process for production of said derivative, as well as its pharmaceutical applications, such as antiinflammatory drugs, antirheumatic drugs, bone metabolic disease drugs, an Interleukin-1 inhibitor, an antioxidant and a bone destruction inhibitor, each having said derivative as its active ingredient.

DETAILED DESCRIPTION

In the case of an unsubstituted naphthyl group, a 1-naphthyl group or 2-naphthyl group is represented. In the case of a naphthyl group having 1 or more substituent groups, a 1-naphthyl group having substituent group(s) at the 2 to 8 positions, or a 2-naphthyl group having substituent group(s) at the 1 position or 3 to 8 positions, is represented. In the case the naphthyl group has substituent group(s), preferable location(s) of the substituent group(s) are the 2 and/or 4 positions when substituted with X and the 5 and/or 6 and/or 8 positions when substituted with Y, in the case of a 1-naphthyl group; and the 1 and/or 4 positions when substituted with X and the 5 and/or 6 and/or 8 positions when substituted with Y, in the case of the 2-naphthyl group. Those halogen atoms used as substituent groups X and Y are fluorine, chlorine, bromine and iodine. Alkyl group (alkyl group indicated hereinafter also has the same meaning) is straight or branched chain alkyl group having 1 to 7 carbon atoms, and for example, methyl, ethyl, propyl, isopropyl, butyl, isobutyl, t-butyl, pentyl, hexyl, cyclohexyl group etc. Alkoxy group is those having 1 to 7 carbon atoms, for example, methoxy, ethoxy, propoxy, isopropoxy, butoxy group etc. Examples of the group:

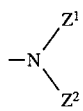

(wherein the alkyl groups of $Z^1$ and $Z^2$ are the same as described above) include amino, methylamino, ethylamino, propylamino, butylamino, dimethylamino, diethylamino, pyrrolidino, piperidino, morpholino, thiomorpholino group etc. Examples of the group:

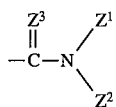

(wherein $Z^1$, $Z^2$, and $Z^3$ are the same as described above) include carbamoyl, thiocarbamoyl, N-methylaminocarbonyl, N,N-dimethylaminocarbonyl, piperidinocarbonyl, pyrrolidinocarbonyl, morpholinocarbonyl group etc. Examples of alkylthio group (wherein the alkyl moiety is the same as the alkyl group described above) include methylthio, ethylthio, propylthio, isopropylthio, cyclopentylthio, cyclohexylthio group etc. Arylthio group is preferably those having 6 to 15 carbon atoms, examples of which include phenylthio, substituted phenylthio groups etc. The acyl (group) of acyloxy, acylamino, acylthio and acyl groups is straight or branched chain group having 2 to 7 carbon atoms, examples of which include acetyl, propanoyl, butanoyl groups etc. Alkenyl group is straight or branched alkenyl group having 2 to 7 carbon atoms, examples of which include vinyl, allyl, 2-propenyl, isopropenyl, butenyl, pentenyl groups etc. Aryl group is preferably those having 6 to 15 carbon atoms, examples of which include phenyl, substituted phenyl, naphthyl groups etc. Cycloalkyl group is those having 3 to 8 carbon atoms, examples of which include cyclopropyl, cyclobutyl, cyclopentyl, cyclohexyl groups etc. Examples of COO alkyl group (wherein the alkyl moiety is the same as the alkyl group previously described) include methoxycarbonyl, ethoxycarbonyl, propoxycarbonyl groups etc.

In the case where A is —($CH_2$)a—(D)b—($CH_2$)c—, and ... represents a single bond, D is sulfur, oxygen, NH, alkyl-substituted N (wherein alkyl is a straight or branched chain alkyl group having 1 to 7 carbon atoms) or $CH_2$; a and c are integers of 0 to 10, and b is 0 or 1 (provided that a=c=0 when b=0). However, more preferably, a, b and c are independently 0 or 1.

Alternatively, in the case where A is —(CH=CH)d—CH=, ... is a double bond, d is an integer of 0 to 2 and B does not exist.

Moreover, in the case where B is other than hydrogen atom and an alkyl group, and D is $CH_2$ and b is an integer other than 1, those compounds wherein c=0 are not preferable since they are chemically unstable. However, even in this case, those compounds wherein a=b=c=0 are preferable because they are stable.

Particularly preferable specific examples include those in which A is S, O, NH, CH=, $CH_2$, $CH_2S$, $CH_2O$, $CH_2NH$, $CH_2CH_2$, $SCH_2$, $SCH_2CH_2$, $SCH_2CH_2CH_2$, $OCH_2$ and $NHCH_2$. In addition, those compounds wherein the naphthyl group is directly bonded to the carbon atom of the methane diphosphonic acid without through the A (namely, the case wherein a=b=c=0) are also included.

Alkyl moiety in the cases wherein B is an alkyl group, monoalkylamino group, dialkylamino group, alkoxy group and trialkylsiloxy group is the same as the alkyl group described above, and the acyl moiety of acylamino and acyloxy groups is the same as the acyl groups described above.

Typical examples of the alkyl group of $R^1$, $R^2$, $R^3$ and $R^4$ include methyl, ethyl, propyl, isopropyl, butyl, isobutyl, t-butyl, pentyl groups and the like.

In the case where $R^1$, $R^2$, $R^3$ and $R^4$ are hydrogen atoms, the phosphonic acid moiety of formula (I) can form a salt with inorganic or organic base. Pharmacologically allowed cations in this case refer to metal cations and ammonium ions $NR_4$ (wherein R is the same as the alkyl group and hydrogen atom of $R^1$ to $R^4$). Particularly preferable metal cations include cations of alkaline metals, such as lithium, sodium, potassium etc, as well as cations of alkaline earth metals, such as magnesium, calcium etc. However, the cation of other metals, such as aluminum, zinc, iron etc, are also included in the present invention. Examples of ammonium ions include ammonium ions of ammonia, primary amines, secondary amines and tertiary amines, as well as quaternary ammonium ions. Examples thereof include ammonium ions of ammonia, methylamine, dimethylamine, trimethylamine, ethylamine, diethylamine, triethylamine, propylamine, dipropylamine, isopropylamine, diisopropylamine, butylamine, dibutylamine, isobutylamine, t-butylamine, monoethanolamine, diethanolamine, triethanolamine etc, as well as tetramethylammonium, tetraethylammonium ions etc. Cations of sodium, potassium, ammonia and alkylamines are particularly preferable. In addition, in $R^1$ to $R^4$, the cations may be identical or different, and those containing a mixture of hydrogen atom and cation are also included in the present invention, examples of which include monocationic salts, dicationic salts and tricationic salts. The methane diphosphonic acid derivatives shown in the general formula (I) is preferably those wherein $R^1$ to $R^4$ are all hydrogen atoms, those wherein three of $R^1$ to $R^4$ are hydrogen atoms, while the other is sodium, those wherein three of $R^1$ to $R^4$ are hydrogen atoms while the other is ammonium, those wherein two of $R^1$ to $R^4$ are hydrogen atoms and the remaining two are sodium, or those wherein two of $R^1$ to $R^4$ are hydrogen atoms while the remaining two are ammonium.

The methane diphosphonic acid derivatives of the present invention can be produced by a process resembling a known process in said field. For example, one of the methane diphosphonic acid derivatives of formula (I) of the present invention (in the case where B is a hydrogen atom) can be produced by the process indicated by the following reaction formula:

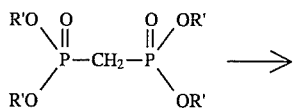

(II)

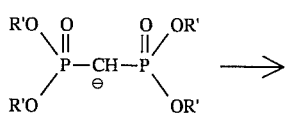

(V)

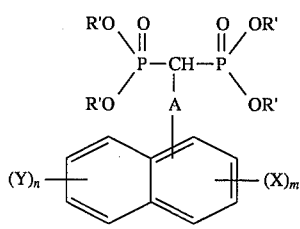

(VI)

R': Lower alkyl
M: Na or Li

The starting substance that is used is a lower alkyl ester of methane diphosphonic acid (II) (wherein the lower alkyl is a straight or branched chain alkyl having 1 to 7 carbon atoms). The corresponding metallized methane diphosphonic ester (y) is formed by reacting the above starting substance with a base such as sodium hydride or alkyl lithium. This is then reacted with various naphthyl-A group introducing agents (wherein naphthyl is:

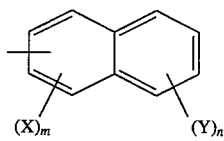

(wherein X, Y, m and n are the same as previously described), and A is the same as previously defined) to form compound (VI). Examples of naphthyl-A group introducing agents that are used include halogen compounds such as naphthyl—$(CH_2)a$—$(D)b$—$(CH_2)c$-halogen [naphthyl—$(CH_2)a$-S-halogen, etc., or a disulfide of naphthyl—$(CH_2)a$-S]$_2$ (wherein D, a, b and c are the same as described above).

The reaction temperature and reaction time vary according to the reagents used. For example, the reaction temperature is between −78° C. and the boiling point of a solvent or solvent mixture, and the reaction time is from 10 minutes to several days.

An example of another synthetic process for a derivative of the methane diphosphonic acid of the general formula (I) is shown by the following reaction formula:

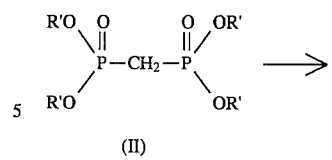

(II)

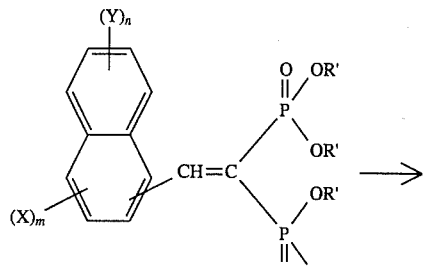

(VII)

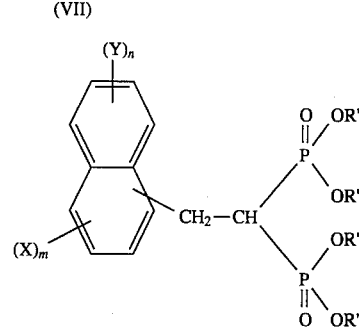

(VIII)

R': Lower alkyl
The aldehyde:

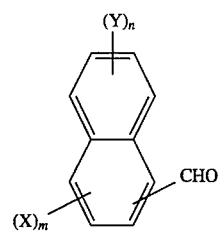

and the lower alkyl ester (II) of methane diphosphonic acid are reacted in as a condensation reaction in the presence of titanium tetrachloride and a tertiary amine such as N-methylmorpholine to obtain compound (VII). Moreover, the double bond that is formed is reduced to obtain compound (VIII).

A methane diphosphonic acid derivative, wherein $R^1$ through $R^4$ are hydrogen atoms, can be obtained from a methane diphosphonic acid derivative wherein $R^1$ through $R^4$ are alkyl groups (phosphonic ester) by hydrolysis and so forth. For example, a phosphonic ester is hydrolyzed either by reacting with an acid such as hydrochloric acid, or treating with trimethylsilylbromide followed by water or alcohol. The methane diphosphonic acid thus obtained can be converted to one of salts thereof by a known process.

In addition, compounds wherein one to three of $R^1$ through $R^4$ are alkyl groups (partial esters of methane diphosphonic acid) obtained by partial hydrolysis of a methane diphosphonic ester or partial esterification of methane diphosphonic acid are also included in the present invention.

In addition, although the P═O bonds in the majority of the methane diphosphonic acid derivatives of the present invention exist in the keto form, there are cases wherein a portion of these bonds may exist in the enol form depending on the chemical properties of the compound itself, solvents and temperature. However, these compounds are also included in the compounds of the present invention.

In addition, in all the reactions, in the case where reactive substituent groups and reactive functional groups for reactions other than the desired reaction are contained, these substituent groups and functional groups must be protected in advance by reagents that allow them to be easily removed.

Those diseases at which compounds of the present invention are directed are inflammatory diseases, pain diseases, skin diseases, respiratory organ diseases, liver diseases, infections, autoimmune diseases, ischemic organ disorders and bone metabolic diseases. For example, the present invention provides a drug having excellent therapeutic and preventive activity against (chronic) articular rheumatism, rheumatoid polyarthritis, osteoarthritis, scapular periarthritis, neck-shoulder-arm syndrome, intervertebral disk disorders, lumbago, tendinitis and peritendinitis, arthrosteitis, stiff and painful shoulder, fibrositis, muscle pain, neuralgia, gout, post-surgical and posttraumatic inflammation and swelling (antiinflammatory drugs, antirheumatic drugs, antiarthritic drugs, analgesics and antipyretics), or psoriasis, asthma, pulmonary sarcoidosis, viral hepatitis, human immunodeficiency viral infections, protozoan infections, ischemic heart disease, ischemic encephalopathy, ischemic hepatitis, arteriosclerosis, osteoporosis, Paget's disease, Bechterew's disease, hypercalcemia and ectopic ossification (bone metabolic disease drugs).

In the case of using the novel methylene or methane diphosphonic acid derivatives of the present invention in the applications of the present invention listed above, said derivatives can be provided for use either as such is or in the form of pharmaceutical compositions mixed with known pharmacologically acceptable carriers, vehicles and so forth. Above-mentioned derivatives may either be given by oral administration in the form of tablets, capsules, powders, granules or pills, or by parenteral administration in the form of injections, syrups, ointments and suppositories. Although the dose varies according to the patient, administration route and symptoms, it is approximately 1 mg to 5 g, and preferably 1 mg to 2 g. This dose may given either orally or parenterally once or several times per 1 day, or once per 1 to 7 days.

EXAMPLES

A more concrete explanation of the present invention will now be provided with reference to the Examples.

Example 1

Tetraethyl 2-naphtbylthiomethanediphosphonate (1)

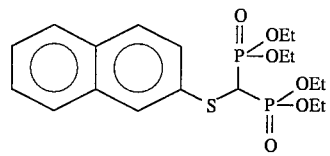

Under an argon atmosphere, a solution of 10.09 g (35 mmol) of tetraethylmethanediphosphonate in dry tetrahydrofuran (100 ml) was cooled to −78° C., and then 22.01 ml (35 mmol) of a solution of n-butyl lithium in hexane [1.59 mol/l] was added thereto, and the mixture was stirred for 30 minutes. Next, a solution of 11.15 g (35 mmol) of 2,2'-dinaphthyl disulfide in dry tetrahydrofuran (75 ml) was added to the mixture, which was then warmed to room temperature, and then stirred for 16 hours. The resulting mixture was poured into ice water and neutralized with 6N hydrochloric acid, and then extracted with ethyl acetate (3×150 ml). The organic layer was washed with water and saturated saline and then dried over anhydrous magnesium sulfate. Next, the solvent was distilled off under reduced pressure, and the resulting residue was purified by column chromatography (developing solvent - ethanol:ethyl acetate=5:95) to obtain 8.82 g of the title compound as a colorless oil. The yield was 57%.

$^1$H-NMR (CDCl$_3$) [ppm]: 1.33 (t, J=7 Hz, 12H), 3.55 (t, J=21 Hz, 1H), 4.00–4.55 (m, 8H), 7.46–7.52 (m, 3H), 7.76–7.83 (m, 3H), 8.07 (S, 1H)

IR (KBr) [cm$^{-1}$]: 2984, 1626, 1589, 1502, 1392, 1257, 1029, 975 MASS (FAB) m/z: 447 (M+H)$^+$ EA (as C$_{19}$H$_{23}$O$_6$P$_2$S) Calculated (%): C 51.12 H 6.33 Found (%): C 51.10 H 6.29

Example 2

2-naphthylthiomethane Diphosphonic Acid (2)

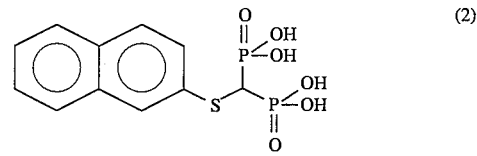

Under an argon atmosphere, to a solution of 8.04 g (18 mmol) of tetraethyl 2-naphthylthiomethane-diphosphonate obtained in Example 1 in dry methylene chloride (100 ml) was added dropwise 27.56 g (180 mmol) of trimethylsilyl bromide at room temperature and then the mixture was stirred at room temperature for 72 hours. After the solvent and the excess trimethylsilyl bromide were distilled off under reduced pressure, the resulting residue was dissolved in a mixed solvent of water:methanol=5:95, and the solution was heated to reflux for 30 minutes, and the solvent was again distilled off under reduced pressure. The resulting residue was crystallized from acetone/methylene chloride and the obtained crystals were recrystallized from the same solvent to obtain the title compound as white crystals. The yield was 86%.

m.p.: 218.5°–219.5° C. (dec)

$^1$H-NMR ( CD$_3$OD ) [ppm]: 3.51 ( t, J=21 Hz, 1H ), 7.42–7.51 (m, 2H), 7.65–7.70 (m, 1H), 7.74–7.87 (m, 3H), 8.10–8.12 (m, 1H)

IR (KBr) [cm$^-$]: 2926, 1657, 1638, 1620, 1151, 973, 812 MASS (FAB) m/z: 335 (M+H)$^+$ EA (as C$_{11}$H$_{12}$O$_6$P$_2$S) Calculated (%): C 39.53 H 3.63 Found (%): C 39.62 H 3.70

Example 3

Tetraethyl 6-methoxy-2-naphthylthiomethanediphosphonate (3)

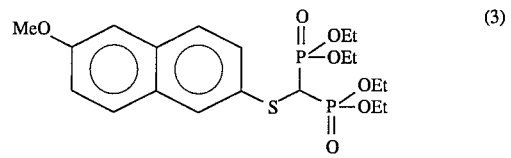

(a) 6,6'-Dimethoxy-2,2'-dinamhthyl disulfide

Under an argon atmosphere, a solution of 10.00 g (28.5 mmol) of 6,6'-dihydroxy-2,2'-dinaphthyl disulfide in dry dimethylformamide (250 ml) was cooled to −23° C., and then 3.42 g (85.5 mmol) of sodium hydride (60% dispersion in mineral oil) was slowly added thereto, and the mixture was stirred until the generation of hydrogen ceased. 12.14 g (85.5 mmol) of methyl iodide was added to the mixture, which was then allowed to stand at room temperature and stirred for 2 hours. The resulting mixture was poured into ice water, and extracted with ethyl acetate (3×150 ml). The organic layer was washed with water and saturated saline and then dried over anhydrous magnesium sulfate. The solvent was distilled off under reduced pressure. The obtained crystals were recrystallized from ethyl acetate/petroleum ether to obtain 9.92 g of 6,6'-dimethoxy-2,2'-dinaphthyl sulfide as orange crystals. The yield was 92%.

m.p.: 125°–126° C.

$^1$H-NMR (CDCl$_3$) [ppm]: 3.89 (s, 6H), 7.00–7.25 (m, 4H), 7.45–7.75 (m, 6H), 7.85–7.95 (m, 2H)

(b) Tetraethyl 6-methoxy-2-naphthylthiomethanediphosphonate

Following the same method as described in Example 1, from 10.09 g (35 mmol) of tetraethyl methanediphosphonate and 13.25 g (35 mmol) of 6,6'-dimethoxy-2,2'-dinaphthyl disulfide was obtained 11.34 g of the title compound as a pale yellow oil. The yield was 68%.

$^1$H-NMR (CDCl$_3$) [ppm]: 1.33 (t, J=7 Hz, 6H), 1.35 (t, J=7 Hz, 6H), 3.48 (t, J=22 Hz, 1H), 3.91 (s, 3H), 4.00–4.45 (m, 8H), 7.00–7.30 (m, 2H), 7.50–7.80 (m, 3H), 8.00–8.10 (m, 1H)

IR (KBr) [cm$^{-1}$]: 2984, 2936, 2910, 1628, 1593, 1390, 1259, 1214, 1023, 975 MASS (FAB) m/z: 477 (M+H)$^+$ EA (as C$_{20}$H$_{30}$O$_7$P$_2$S) Calculated (%): C 50.42 H 6.36 Found (%): C 50.65 H 6.42

Example 4

6-Methoxy-2-naphthylthiomethanediphosphonic Acid (4)

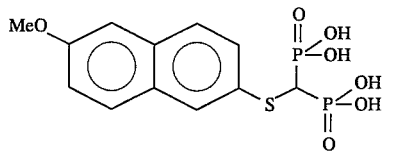

Following the same method described as in Example 2, 7.15 g (15 mmol) of tetraethyl 6-methoxy-2-naphthylthiomethanediphosphonate obtained in Example 3 in dry methylene chloride was treated with trimethylsilyl bromide, and then hydrolyzed to obtain 4.21 g of the title compound as white crystals. The yield was 77%.

m.p.: 234°–235° C. (dec)

$^1$H-NMR (CD$_3$OD) [ppm]: 3.37 (t, J=21 Hz, 1H), 3.90 (s, 3H), 7.12–7.23 (m, 2H), 7.65–7.75 (m, 3H), 8.05–8.09 (m, 1H)

IR (KBr) [cm$^{-1}$]: 2920, 1628, 1466, 1214, 1125, 994, 924, 911 MASS (FAB) m/z: 365 (M+H)$^+$ EA (as C$_{12}$H$_{14}$O$_7$P$_2$S) Calculated (%): C 39.57 H 3.88 Found (%): C 39.55 H 3.79

Example 5

Tetraethyl 6-hydroxy-2-naphthylthiomethanediphosphonate (5)

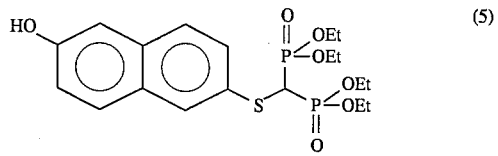

(a) 6,6'-Di(t-butyldimethylsiloxy)-2,2'-dinaphthyl disulfide

Under an argon atmosphere, a solution of 10.00 g (28.5 mmol) of 6,6'-dihydroxy-2,2'-dinaphthyl disulfide and 9.70 g (140 mmol) of imidazole in dimethylformamide (150 ml) was cooled to 0° C., and a solution of 12.89 g (85.5 mmol) of t-butyldimethylchlorosilane in dry dimethylfomamide (50 ml) was added thereto, and the mixture was warmed to room temperature and then stirred for 3 hours. The resulting mixture was poured into ice water, and extracted with ethyfl acetate (3×150 ml). The organic layer was washed with water and saturated saline and then dried over anhydrous magnesium sulfate. The solvent was distilled off under reduced pressure. The obtained residue was purified by column chromatography (developing solvent - ethyl acetate:n-hexane =5:95) to obtain the title disulfide compound as a pale yellow oil. The yield was 99%.

$^1$H-NMR (CDCls) [ppm]: 0.23 (s, 6H), 1.00 (s, 9H), 6.95–7.20 (m, 2H), 7.45–7.70 (m, BH), 7.85–7.95 (m, 1H)

(b) Tetraethyl 6-hydroxy-2-naphthylthiomethanediphosphonate

Following the same method as described in Example 1, a reaction between 10.09 g (35 mmol) of tetraethyl methanediphosphonate and 13.25 g (35 mmol) of 6,6'-di(t-butyldimethylsiloxy)-2,2'-dinaphthyl disulfide was carried out. After evaporation of the solvent of the reaction mixture, the resulting residue was dissolved in a mixed solvent of 6N hydrochloric acid:methanol=1:20, heated at 50° C. for 30 minutes, and the solvent was again distilled off under reduced pressure. The obtained residue was purified by column chromatography (developing solvent - ethanol:ethyl acetate=5:95) to obtain 10.02 g of the title compound as a pale yellow oil which slowly crystallized. The yield was 62%.

m.p.: 85.5°–86.5° C.

$^1$H-NMR(CDCl$_3$) [ppm]: 1.35 (t, J=7 Hz, 12H), 3.50 (t, J=22 Hz, 1H), 4.05–4.65 (m, 8H), 6.95–7.20 (m, 2H), 7.25–7.70 (m, 3H), 7.90–8.05 (m, 1H), 8.95 (brs, 1H)

IR (KBr) [cm$^{-1}$]: 3148, 2984, 1626, 1392, 1232, 1212, 1027 MASS (FAB) m/z: 463 (M+H)$^+$ EA (as C$_{19}$H$_{28}$O$_7$P$_2$S) Calculated (%): C 49.35 H 6.12 Found (%): C 49.39 H 6.11

Example 6

6-Hydroxy-2-naphthylthiomethanediphosphonic Acid (6)

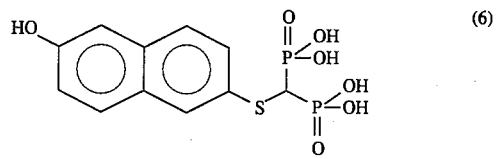

Following the same method as in Example 2, 7.15 g (15 mmol) of the tetraethyl 6-hydroxy-2-naphthylthiomethanediphosphonate obtained in Example 5 was treated with trimethylsilyl bromide, and then hydrolyzed to obtain 4.21 g of the title compound as white crystals.

The yield was 75%.

m.p.: 210°–211° C. $^1$H-NMR (D$_2$O) [ppm]: 3.51 (t, J=20 Hz, 1H), 7.02–7.13 (m, 2H), 7.48–7.55 (m, 1H), 7.55–7.62 (m, 1H), 7.63–7.69 (m, 1H), 7.90–7.97 (m, 1H)

IR (KBr) [cm$^{-1}$]: 3570, 3164, 1636, 1506, 1135, 1046, 939, 919 MASS (FAB) m/z: 351 (M+H)$^+$ EA (as C$_{11}$H$_{12}$O$_7$P$_2$S) Calculated (%): C 37.73 H 3.46 Found (%): C 37.80 H 3.55

Example 7

Tetraethyl 1-naphthylthiomethanediphosphonate (7)

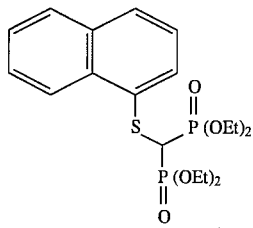

(7)

(a) 1,1'-dinaphthyl disulfide

Under an argon atmosphere, to a solution of 22.67 g (100.0 mmol) of 1-naphthalenesulfonyl chloride in dry methylene chloride (250 ml) was slowly added 100.0 g (500.0 mmol) of iodotrimethylsilane, and the mixture was stirred for 6 hours. The resulting mixture was poured into an saturated aqueous solution of sodium bicarbonate, and extracted with methylene chloride (3×150 ml). The organic layer was washed with a saturated aqueous solution of sodium thiosulfate until the iodine coloring disappeared, and further washed with water and saturated saline, and then dried over anhydrous magnesium sulfate. The solvent was distilled off under reduced pressure, and the obtained crystals were recrystallized from ethyl acetate/n-hexane to obtain 12.43 g of the title compound as pale yellow crystals. The yield was 78%.

m.p.: 85°–86° C.

$^1$H-NMR (CDCl$_3$) [ppm]: 7.15–8.00 (m, 12H), 8.20–8.45 (m, 2H)

(b) Tetraethyl 1-naphthylthiomethanediphosphonate

Following the same method as described in Example 1, from 10.09 g (35 mmol) of tetraethyl methanediphosphonate and 11.15 g (35 mmol) of 1,1'-dinaphthyl disulfide was obtained 9.38 g of the title compound as a pale yellow oil. The yield was 60%.

$^1$H-NMR (CDCl$_3$) [ppm]: 1.30 (t, J=7 Hz, 12H), 3.55 (t, J=21 Hz, 1H), 3.95–4.45 (m, 8H), 7.30–7.75 (m, 3H), 7.75–8.10 (m, 3H), 8.55–8.75 (m, 1H)

IR (KBr) [cm$^{-1}$]: 3434, 2984, 2934, 2910, 1506, 1444, 1.255, 1164, 1098, 1013, 971 MASS (FAB) m/z: 447 (M+H)$^+$ EA (as C$_{19}$H$_{28}$O$_6$P$_2$S) Calculated (%): C 51.12 H 6.33 Found (%): C 51.33 H 6.19

Example 8

1-Naphthylthiomethanediphosphonic Acid (8)

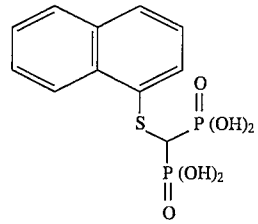

Following the same method as described in Example 2, 6.70 g (15 mmol) of tetraethyl 1-naphthylthiomethanediphosphonate was treated with trimethylsilyl bromide, and then hydrolyzed to obtain 3.92 g of the title compound as white crystals. The yield was 78%.

m.p.: 241°–242° C. (dec)

$^1$H-NMR (CD$_3$OD) [ppm]: 3.45 (t, J=21 Hz, 1H), 7.30–7.70 (m, 3H), 7.75–8.10 (m, 3H), 8.60–8.80 (m, 1H)

IR (KBr) [cm$^{-1}$]: 2910, 2892, 1506, 1185, 1141, 1006, 932 MASS (FAB) m/z: 335 (M+H)$^+$ EA (as C$_{11}$H$_{12}$O$_6$P$_2$S) Calculated (%): C 39.53 H 3.63 Found (%): C 39.44 H 3.70

Example 9

Tetraethyl 2-[3-methoxy-4-hydroxy-1-naphtbyl] ethenylidene-1,1-diphosphonate

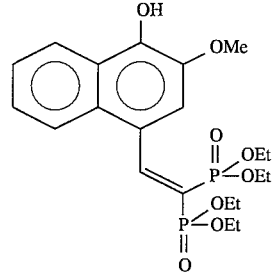

Under an argon atmosphere, 55 ml of dry tetrahydrofuran was cooled to 0° C., and a solution of 20.49 g (108 mmol) of titanium tetrachloride in dry methylene chloride (15 ml) was slowly added dropwise thereto over a period of 15 minutes. To the resulting mixture were added a solution of 15.57 g (54 mmol) of tetraethyl methanediphosphonate in dry tetrahydrofuran (40 ml) and a solution of 10.92 g (54 mmol) of 3-methoxy-4-hydroxy-1-naphthaldehyde in dry tetrahydrofuran (40 ml), and the mixture was stirred for 10 minutes. After stirring, a solution of 21.85 g (216 mmol) of N-methylmorpholine in dry tetrahydrofuran (40 ml) was slowly added dropwise thereto over a period of 30 minutes so as to maintain the temperature below 5° C. The resulting mixture was stirred for 30 minutes and then warmed to room temperature and stirred for 5 hours. The reaction mixture was poured into ice water and extracted with ethyl acetate (3×150 ml). The organic layer was successively washed with a saturated aqueous solution of sodium bicarbonate, with water and with saturated saline, and then dried over anhydrous magnesium sulfate, after which the solvent was distilled off under reduced pressure. The obtained residue was purified by column chromatography (developing solvent - ethanol:ethyl acetate=5:95), and then recrystallized from mixed solvent of ethyl acetate/diethyl ether, to obtain 18.37 g of the title compound as yellow crystals. The yield was 72%.

m.p.: 115.5°–116.5° C.

$^1$H-NMR (CD$_3$Cl) [ppm]: 1.02 (t, J=7 Hz, 6H), 1.42 (t, J=7 Hz, 6H), 3.30–4.50 (m, 8H), 4.04 (s, 3H), 6.90 (brs, 1H), 7.30–7.65 (m, 2H), 7.70–7.95 (m, 1H), 8.10–8.35 (m, 1H), 8.20 (s, 1H), 8.35 (dd, J=24.46 Hz, 1H)

IR (KBr) [cm$^{-1}$]: 3190, 2990, 1553, 1363, 1247, 1226, 1036, 996 MASS (FAB) m/z: 473 (M+H)$^+$ EA (as C$_{21}$H$_{30}$O$_8$P$_2$) Calculated (%): C 53.39 H 6.41 Found (%): C 53.33 H 6.50

Example 10

2-[3-Methoxy-4-hydroxy-1-naphthyl]ethenylidene-1,1-diphosphonic Acid

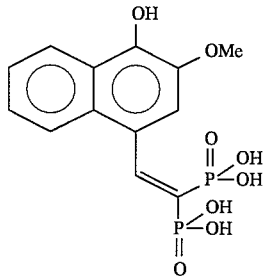

Following the same method as described in Example 2, 9.45 g (20 mmol) of the tetraethyl 2-[3-methoxy-4-hydroxy-1-naphthyl]ethenylidene-1,1-diphosphonate obtained in Example 9 was treated with trimethylsilyl bromide, and then hydrolysis was effected to obtain 4.97 g of the title compound as yellow crystals. The yield was 69%.

m.p.: 123°–124° C. (dec)

$^1$H-NMR (CD$_3$OD) [ppm]: 4.01 (s, 3H), 7.37–7.52 (m, 2H), 7.85–7.93 (m, 1H), 8.12 (s, 1H), 8.15–8.23 (m, 1H), 8.73 (dd, J=28.46 Hz, 1H)

IR (KBr) [cm$^{-1}$]: 3450, 1603, 1574, 1363, 1125, 1058, 1009 MASS (FAB) m/z: 361 (M+H)$^+$ EA (as C$_{13}$H$_{14}$O$_8$P$_2$) Calculated (%): C 43.35 H 3.93 Found (%): C 43.20 H 3.82

Example 11

Tetraethyl 2-[3-methoxy-4-hydroxy-1-naphthyl]ethane-1,1-diphosphonate

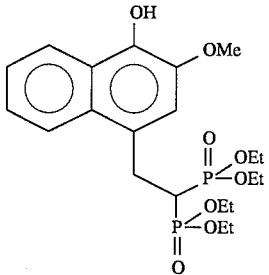

Under an argon atmosphere, to a solution of 8.50 g (18 mmol) of the tetraethyl 2-[3-methoxy-4-hydroxy-1-naphthyl]ethenylidene-1,1-diphosphonate obtained in Example 9 in dry tetrahydrofuran (120 ml) was slowly added 2.72 g (72 mmol) of sodium borohydride. The resulting mixture was warmed to 50° C. and stirred for 30 minutes. Next, the mixture was cooled to 0° C., a saturated aqueous solution of ammonium chloride was added thereto until hydrogen was no longer evolved, and the mixture was neutralized with 1N hydrochloric acid, and then extracted with ethyl acetate (3×150 ml). The organic layer was successively washed with a saturated aqueous solution of sodium bicarbonate, with water and with saturated saline, and then dried over anhydrous magnesium sulfate, after which the solvent was distilled off under reduced pressure. The obtained residue was purified by column chromatography (developing solvent-ethanol:ethyl acetate=5:95), to obtain 8.28 g of the title compound as a pale yellow oil. The yield was 98%.

$^1$H-NMR (CD$_3$Cl) [ppm]: 1.22 (t, J=7 Hz, 6H), 1.24 (t, J=7 Hz, 6H), 2.87 (tt, J=6.23 Hz, 1H), 3.70–4.50 (m, 8H), 3.71 (dt, J=6.16 Hz, 2H), 3.95 (s, 3H), 6.60 (s, 1H), 7.30–7.57 (m, 2H), 7.35 (s, 1H), 7.95–8.05 (m, 1H), 8.05–8.15 (m, 1H)

IR (KBr) [cm$^{-1}$]: 3248, 2986, 1630, 1603, 1586, 1479, 1367, 1247, 1025, 975 MASS (FAB) m/z: 475 (M+H)$^+$ EA (as C$_{21}$H$_{32}$O$_8$P$_2$) Calculated (%): C 53.17 H 6.81 Found (%): C 53.23 H 6.96

Example 12

2-[3-Methoxy-4-hydroxy-1-naphthyl]ethane-1,1-diphosphonic Acid

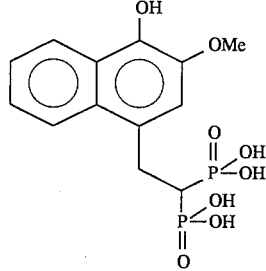

Following the same method as described in Example 2, 7.12 g (15 mmol) of the tetraethyl 2-[3-methoxy-4-hydroxy-1-naphthyl]ethane-1,1-diphosphonate obtained in Example 11 was treated with trimethylsilyl bromide, and then hydrolysis was effected to obtain 3.64 g of the title compound as pale yellow crystals. The yield was m.p.: 231°–232° C. (dec)

$^1$H-NMR (CD$_3$OD) [ppm]: 2.68 (tt, J=6.23 Hz, 1H), 3.65 (dt, J=6.16 Hz, 2H), 3.96 (s, 3H), 7.33–7.40 (m, 2H), 7.42 (s, 1H), 8.04–8.11 (m, 1H), 8.11–8.18 (m, 1H)

IR (KBr) [cm$^{-1}$]: 3324, 2906, 1638, 1475, 1402, 1278, 1176, 1033 MASS (FAB) m/z: 363 (M+H)$^+$ EA (as C$_{13}$H$_{16}$O$_8$P$_2$) Calculated (%): C 43.11 H 4.46 Found (%): C 43.02 H 4.45

Example 13

Tetraethyl 2-[3-methylthio-4-hydroxy-1-naphthyl]ethenylidene-1,1-diphosphonate

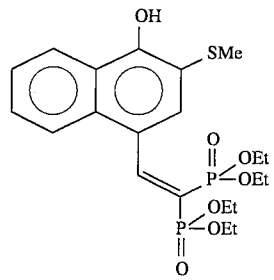

Following the same method as described in Example 9, from 14.42 g (50 mmol) of tetraethyl methanediphosphonate and 10.91 g (50 mmol) of 3-methylthio-4-hydroxy-1-naphthaldehyde was obtained 18.32 g of the title compound as yellow crystals. The yield was 75%.

m.p.: 106°–107° C.

$^1$H-NMR (CD$_3$Cl) [ppm]: 1.03 (t, J=7 Hz, 6H), 1.45 (t, J=7 Hz, 6H), 2.43 (s, 3H), 3.70–4.50 (m, 8H), 7.50 (s, 1H), 7.50–7.70 (m, 2H), 7.70–7.90 (m, 1H), 8.14 (s, 1H), 8.20–8.45 (m, 1H), 8.80 (dd, J=28.46 Hz, 1H)

IR (KBr) [cm$^{-1}$]: 2990, 1568, 1396, 1313, 1251, 1212, 1046, 982 MASS (FAB) m/z: 489 (M+H)$^+$ EA (as C$_{21}$H$_{30}$O$_7$P$_2$S) Calculated (%): C 51.64 H 6.20 Found (%): C 51.55 H 6.33

Example 14

Tetraethyl 2-[3-methylthio-4-hydroxy-1-naphthyl]ethane-1,1-diphosphonate

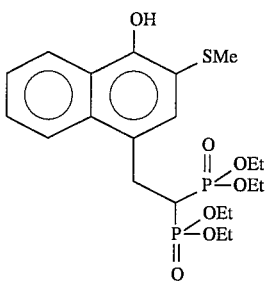

Following the same method as described in Example 11, 8.79 g (18 mmol) of tetraethyl 2-[3-methylthio-4-hydroxy-1-naphthyl]ethenylidene-1,1-diphosphonate was reduced using 2.72 g (72 mmol) of sodium borohydride to obtain 8.73 g of the title compound as a pale yellow oil. The yield was 99%.

$^1$H-NMR (CD$_3$Cl) [ppm]: 1.22 (t, J=7 Hz, 6H), 1.26 (t, J=7 Hz, 6H), 2.37 (s, 3H), 2.82 (tt, J=6.23 Hz, 1H), 3.65 (dt, J=6.16 Hz, 2H), 3.80–4.35 (m, 8H), 7.23 (s, 1H), 7.35–7.70 (m, 2H), 7.55 (s, 1H), 7.93–8.18 (m, 1H), 8.18–8.42 (m, 1H)

IR (KBr) [cm$^{-1}$]: 3216, 2986, 2928, 1572, 1450, 1388, 1249, 1019, 975 MASS (FAB) m/z: 491 (M+H)$^+$ EA (as C$_{21}$H$_{32}$O$_7$P$_2$S) Calculated (%): C 51.42 H 6.60 Found (%): C 51.66 H 6.73

Example 15

2-[3-Methylthio-4-hydroxy-1-naphthyl]ethane-1,1-diphosphonic Acid

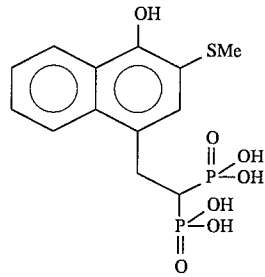

Following the same method as described in Example 2, 7.36 g (15 mmol) of tetraethyl 2-[3-methylthio-4-hydroxy-1-naphthyl]ethane-1,1-diphosphonate was treated with trimethylsilyl bromide, and then hydrolysis was effected to obtain 4.03 g of the title compound as pale yellow crystals. The yield was 71%.

m.p.: 195°–196° C. (dec)

$^1$H-NMR (CD$_3$OD) [ppm]: 2.39 (s, 3H), 2.68 (tt, J=6.23 Hz, 1H), 3.63 (dt, J=6.16 Hz, 2H), 7.35–7.70 (m, H), 7.57 (s, 1H), 8.00–8.40 (m, 2H)

IR (KBr) [cm$^{-1}$]: 3386, 1578, 1392, 1276, 1210, 1162, 1079, 1013 MASS (FAB) m/z: 379 (M+H)$^+$ EA (as C$_{13}$H$_{16}$O$_7$P$_2$S) Calculated (%): C 41.28 H 4.27 Found (%): C 41.33 H 4.38

Example 16

Adjuvant Arthritis Test

When a tubercule bacillus adjuvant is injected into rats, multiple arthritis, similar to human chronic articularheumatism, is induced. The anti-inflammatory, anti-rheumatic and bone metabolism-improving effects of the compounds of the present invention were investigated according to the following procedure using this adjuvant arthritis model.

0.1 mg of dry, dead tubercule bacilli (*Mycobacterium butyricum*) cells was suspended in 0.1 ml of liquid paraffin, and intracutaneously injected into the left bind paw of 7-week-old female Lewis rats. The compounds obtained in the Examples were dissolved in sterilized distilled water, and subcutaneously administered at a proportion of 20 mg per kilogram of weight for 2 consecutive weeks, from the 8th to the 21st day after injection of the adjuvant. During that time, the volumes of the left and right paws of the rats were measured plethysmographically, and edema density was calculated according to the following equation.

$$\text{Edema density} = \frac{[\text{Paw volume (ml) on day 16, 17 or 21} - \text{paw volume (ml) on day 7}]}{[\text{Paw volume (ml) on day 7}]} \times 100$$

Furthermore, inhibition rate of edema was determined according to the following equation, and are shown in Table 1.

$$\text{Inhibition rate of edema} = \frac{[\text{Edema density of control group} - \text{edema density of compound-administered group}]}{[\text{Edema density of control group}]} \times 100$$

The rats were sacrified on day 22, and soft X-ray radiographs were taken of the left and right hind legs. The degree of osteoclasia at 5 locations on the left and right hind legs was evaluated based on the soft X-ray radiographs and assigned points from a system of 5 grades, and the total thereof was used as the osteoclasia rating. Furthermore, the inhibition rate of osteoclasia were calculated according to the following equation, and are shown in Table 1.

Inhibition rate of osteoclasia =

$$\frac{[\text{Average osteoclasia rating of control group} - \text{average osteoclasia rating of compound-administered group}]}{[\text{Average osteoclasia rating of control group}]} \times 100$$

The obtained results were indicated with "*" in cases where, based on the Student t-test and the Tukie multiple comparison method, the level of significance was P<0.001, with "" in cases where the level of significance was P<0.01, and with "*" in cases where the level of significance was P<0.05 with respect to the control group to which was administered sterilized distilled water alone.

As is clear from Table 1, foot edema and osteoclasia due to primary and secondary inflammation of adjuvant arthritis were suppressed by administration of the compounds according to the present invention.

J774–1 cells were cultured in an RPMI-1640 culture medium containing 10% fetal calf serum and 50 μM of 2-mercaptoethanol, and prepared to a cell concentration of $2\times10^5$ cells/ml. The cell suspension was distributed into a 24-well plate to 1 ml per well, and cultured for 30 minutes. LPS was then added thereto to a final concentration of 1 μg/ml, and at the same time the compounds obtained in the Examples dissolved in sterilized distilled water were added to a concentration of 100 μM. After 24 hours' culturing at 37° C. in a 5% $CO_2$ environment, the supernatant was recovered, centrifuged to remove the cell fragments, etc., and then passed through a 0.22 μm filter for sterilization.

The measurement of IL-1 activity was made by measuring the proliferation of thymocytes in male C3H/He J mice. In fact, 4 to 6-week-old male C3H/He J mouse was used, and the thymus was taken. The thymus was dissociated in an RPMI-1640 culture medium containing 10% fetal calf serum and 50 μM of 2-mercaptoethanol, and a cell suspension was prepared to a concentration of $2\times10^7$ cells/ml. Phytohemagglutinin was added to the cell suspension to a final concentration of 1%, and this was used as the T cell suspension.

A two-fold serial dilution was made of the above obtained sample in a 96-well multiplate to a volume of 50 μl per well, and 50 μl of the T cell suspension was added to each well. The T cells were cultured for 72 hours, and the IL-1 activity was determined by the rate of cell proliferation. The cell

TABLE 1

| Compounds | Number of cases | Inhibition rate of edema with respect to control group (%) | | | | Inhibition rate of osteoclasia with respect to control group (%) |
|---|---|---|---|---|---|---|
| | | 16th or 17th day | | 21th day | | |
| | | Left | Right | Left | Right | 22nd day |
| Compound of Example 2 | 6 | 76.8*** | 35.2** | 94.5*** | 44.3*** | 75.2** |
| Compound of Example 4 | 6 | 80.0*** | 40.8** | 93.0*** | 33.4*** | 55.2** |
| Compound of Example 6 | 6 | 85.6*** | 31.8* | 117.3*** | 39.9** | 60.3** |

The measurement of foot edema was made on the 17th and 21st days for the compounds in Examples 2 and 4, and on the 16th and 21st days for the compound in Example 6.

Example 17

Effect Against Production of IL-1 by Mouse Macrophage Cell Line J774–1

Macrophages, one type of lymphocytes, ingest invading microorganisms, blood cell fragments, etc., present antigens to B cells, and release active oxygen to digest foreign bodies, as a foreign body-removal mechanism. At this time the macrophages release a number of cytokines, including IL-1 which causes fever, inflammation, chondroclasia, osteoclasia, activation of leukocytes, damage to vascular endothelial cells, etc., and is also known to exhibit various effects by inducing the production of other cytokines.

Mouse macrophage cell line J774–1 is selected from cells exhibiting high production of IL-1, and it is known to produce IL-1 when stimulated by LPS. With this cell line, the inhibitory effects to IL-1 production of the compounds according to the present invention were determined by the following procedure.

proliferation was calculated using as the value of the absorbance at 570 nm of the pigment produced upon reduction of 3-[4,5-dimethylthiazole-2-yl]-2,5-diphenyltetrazolium bromide by the mitochondria of the viable cells, added at 4 hours prior to completion of the culturing, with 100% proliferation defined as the maximum proliferation of T cells induced by recombinant human IL-1, 0% defined as proliferation with no addition of IL-1, and the units of the sample defined as the degree of dilution of the sample which caused 50% proliferation of the T cells.

At this time, the inhibition rates of the compounds according to the present invention against IL-1 production by J774-1 cells stimulated with 1 μg/ml of LPS was calculated using the following equation. The results are shown in Table 2.

$$\text{IL-1 production inhibition rate} = \frac{\text{IL-1 units of control group} - \text{IL-1 units of compound-treated group}}{\text{IL-1 units of control group}} \times 100(\%)$$

(Note: The units are "units/ml")

TABLE 2

| | IL-1 production inhibition rate with respect to control group |
|---|---|
| Compound of Example 2 | 41.7% |

Example 18

Rabbit cartilage cells are separated from knee joint and cultured. When they are stimulated with IL-1, proteoglycan, the main constituent glycoprotein of cartilage cells, is degraded. Using this consequence as an index, the IL-1-inhibiting effects of the compounds according to the present invention were determined in the following manner.

Three-week-old male New Zealand white rabbits weighing 250 g–300 g were sacrified under diethyl ether anesthesia, and their knee joints were separated. The cartilaginous sections were cut out from the knee joint with a scalpel, and then immersed in CMF solution containing 0.14M sodium chloride, 4 mM potassium chloride, 0.4 mM sodium dihydrogen phosphate, 12 mM sodium bicarbonate, 0.2 mM potassium dihydrogen phosphate and 11 mM glucose. The cartilage was placed in 0.1% EDTA and incubated at 37° C. for 20 minutes. The supernatant was removed off, 0.15% trypsin was added to the mixture, and then that was incubated at 37° C. for 60 minutes. The mixture was washed 3 times with CMF solution, and then placed in 15% collagenase and further treated at 37° C. for 105 minutes. The cartilage cells were isolated from the cartilaginous tissue fragments by pipetting and pushed through 120 μm nylon mesh, and then subjected to centrifugation at 4° C., 500 g for 7 minutes to obtain the cartilage cells. The cells were washed 3 times, and then suspended in Dulbecco MEM culture medium containing 10% fetal calf serum, to concentration of $1.2 \times 10^5$ cells/ml. The cells were distributed into a 48-well plate to 250 μl per well and cultured for 5 days until confluence. Then, the culture solution was exchanged with Dulbecco MEM medium containing 0.3% fetal calf serum. After the further incubation for 24 hours, S-labelled inorganic sulfuric acid was added to concentration of 185 kilobecquerels, and the incubation was continued for further 24 hours. The cells were washed 3 times with Dulbecco MEM medium, the culture medium was exchanged with a BGjb medium containing 0.1% bovine serum albumin, and recombinant human IL-1β was added to a concentration of 30 units/mi. At the same time, the compounds according to the present invention were dissolved in sterilized distilled water, and added to a final concentration of 100 μM. At 24 hours after IL-1 stimulation, the culture supernatant and the cell layer were collected.

The cell layer was decomposed by adding 200 μg of Pronase E and treatment at 37° C. for 24 hours. To the culture supernatant were successively added 0.05 ml of 0.1 mg/ml chondroitin sulfate, 0.5 ml of 2 mM magnesium sulfate, 0.5 ml of a buffer solution (pH 7.8) containing 5 mM calcium chloride and 0.2M Tris-HCl and 0.5 ml of a solution of 1% cetyl pyridinium chloride and 20 mM sodium chloride, and the proteoglycan which precipitated upon treatment at 37° C. for 2 hours was collected into a glass filter, a liquid scintillator was added thereto, and the count was made using a liquid scintillation counter.

To the digested cell layer solution were successively added 0.05 ml of 0.1 mg/ml chondroitin sulfate, 0.5 ml of 2 mM magnesium sulfate and 0.5 ml of a solution of 1% cetyl pyridinium chloride and 20 mM sodium chloride, and the proteoglycan which precipitated upon treatment at 37° C. for 2 hours was harvested into a glass filter, a liquid scintillator was added thereto, and the count was made using a liquid scintillation counter.

Each of the obtained counts was divided by the count at the initial addition of inorganic sulfuric acid, and expressed as a percentage. The obtained results were indicated with "$$" in cases where, using the Student ttest, the level of significance was P<0.01 with respect to the non-stimulated control group and with "**" in cases where the level of significance was P<0.01 with respect to the IL-1-stimulated control group. As shown in Table 3, the compounds according to the present invention inhibited the degradation of proteoglycan from the IL-1-stimulated cell layer, and are thus effective as IL-1-inhibiting agents.

TABLE 3

| | Supernatant | Cell layer |
|---|---|---|
| Not stimulated | 0.63 ± 0.035 | 0.45 ± 0.036 |
| IL-1-stimulated | 1.06 ± 0.018$$ | 0.11 ± 0.004$$ |
| IL-1-stimulated and compound-treated (Compound of Example 2) | 0.78 ± 0.015** | 0.31 ± 0.011** |

Example 19

Neutrophils are known to ingest foreign bodies for their removal and to produce active oxygen and digestive enzymes, as a biological defense mechanism. However, during chronic inflammation, etc., the active oxygen and digestive enzymes produced by neutrophils also damage normal tissue, and are thought to further reinforce inflammation. Here, the effects of the compounds according to the present invention against the release of active oxygen from neutrophils were determined in the following manner.

Using 3.8% sodium citrate as an anticoagulant, 50 ml of blood was taken from a human vein. The blood was mixed with the same volume of a solution of 2% dextran and physiological saline, and the mixture was shaken several times and then allowed to stand at 37° C. for 30 minutes. The upper layer was separated off and overlayered onto the same volume of a Ficoll-Paque solution. The precipitate resulting from 30-minutes' centrifugation at 20° C. 1400 rpm was taken, the cells were resuspended in Hanks' balanced salt solution, centrifugation was performed at 20° C., 1000 rpm for 5 minutes, and the precipitated cells were washed. The contaminating erythrocytes were eliminated by subjection to osmotic shock, and finally the neutrophils were suspended in Hanks' balanced salt solution to a concentration of $1 \times 10^6$ cells/ml. Of these neutrophils, $1 \times 10^5$ cells were incubated at 37° C. with $10^9$M of the stimulant, formyl-methionyl-leucyl-phenylalanine (fMLP), and at the same time the compounds according to the present invention were added thereto and the production of active oxygen was measured. For the measurement of the active oxygen, 2-methyl-6-phenyl-3,7-dihydroimidazo [1,2a]pyrazine-3-one (CLA) was reacted therewith resulting in excited carbonyl compounds, and utilizing the phenomenon whereby light is emitted at 380 nm during their transition to ground state, the maximum luminescence intensity was measured with a luminometer. The inhibition rate against active oxygen production was calculated according to the following equation. The results are shown in Table 4.

Active oxygen production inhibition rate =

$$\frac{\text{Maximum luminescence intensity of control group (RLU/sec)} - \text{maximum luminescence intensity of compound-treated group (RLU/sec)}}{\text{Maximum luminescence intensity of control group (RLU/sec)}} \times 100$$

TABLE 4

| | | Active oxygen production inhibition rate |
|---|---|---|
| Compound of Example 2 | 10 μm | 29.4 ± 6.58% |

Example 20

In conditions of osteoporosis, it is thought that the balance between bone formation and bone resorption is lost, with bone resorption being accelerated. Bone resorption is thought to occur due to the activation and increase in the number of osteoclasts, and a model thereof is an experiment in which mouse osteocytes are planted on dentin slices, causing bone resorption due to the stimulation of active-type vitamin $D_3$. Using this model, the bone resorption-inhibiting effects of the compounds according to the present invention were determined.

The femurs and tibias were separated from 10 to 15-day-old ICR mice, and minced in an α-MEM culture medium containing 5% fetal calf serum, and an osteoclast suspension was prepared containing bone marrow cells and bone matrix. The large bone fragments were removed using a nylon mesh, and the viable cells were stained using trypan blue staining, while the osteoclasts were stained using tartaric acid-resistant acidic phosphatase staining, and a cell suspension was prepared which contained the osteoclasts at a proportion of about 0.05–0.1%. The dentin was cut to thicknesses of 150 μm using a low-speed rotating diamond cutter, and punched with a puncher to the size of wells of a 96-well plate. The dentin slices were placed in a 96-well plate, and the cell suspension prepared as described above was placed thereupon to a concentration of 500 osteoclasts per well. As a stimulant, 10 nM active-type vitamin $D_3$ was added thereto, and at the same time the preparations according to the present invention were added thereto to concentrations of 10 μM and 100 μM. The cells were cultured at 37° C. in 10% $CO_2$ environment, and after 4 days' culture the resorption pits which formed on the dentin slices were stained with hematoxylin, and then observed under a microscope and counted. The rate of inhibition of resorption pit formation was calculated according to the following equation.

$$\text{Inhibition rate} = \frac{\text{Number of resorption pits occurring in control group} - \text{number of resorption pits occurring in compound group}}{\text{Number of resorption pits occurring in control group}} \times 100$$

The results are shown in Table 5. The results were indicated with "*" in cases where, based on statistical calculation using the Student t-test, the level of significance was P<0.05 and with "**" in cases where the level of significance was P<0.01 with respect to the active-type vitamin $D_3$-stimulated control group.

TABLE 5

| | | Inhibition rate with respect to control (%) |
|---|---|---|
| Compound of Example 2 | 10 μM | 18.8 ± 6.23 |
| | 100 μM | 92.1 ± 0.43** |
| Compound of Example 4 | 10 μM | 47.7 ± 2.18* |
| | 100 μM | 94.8 ± 1.04** |
| Compound of Example 6 | 10 μM | 30.6 ± 12.5 |
| | 100 μM | 90.8 ± 1.33** |

[Industrial Applicability]

The compounds according to the present invention possess anti-IL-1, anti-oxidation and anti-bone resorption effects, etc. and are thus useful as anti-inflammatory agents, analgesics, antirheumatic agents, agents for bone metabolism disorders, agents for autoimmune diseases, agents for infections, agents for dermatologic diseases, antiallergic agents, antioxidants and therapies for ischemic organ damage.

We claim:

1. A methanediphosphonic acid derivative represented by the general formula (I):

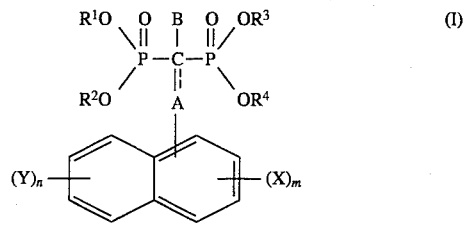

wherein X and Y represent substitution groups on the naphthyl group, and represent a halogen atom, nitro group, nitrile group, alkyl group, alkoxy group, trifluoromethyl group, the group:

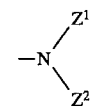

provided that $Z^1$ and $Z^2$ represent, independently of each other, a hydrogen atom or an alkyl group, or $Z^1$ or $Z^2$ may form a ring comprising carbon atoms or a ring comprising carbon atoms and hetero atoms, the group:

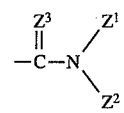

provided that $Z^1$ and $Z^2$ are the same as above, and $Z^3$ represents oxygen or sulfur, thiol group, hydroxyl group, alkylthio group, arylthio group, acyloxy group, acylamino group, acylthio group, acyl group, alkenyl group, aryl group, cycloalkyl group, COOH group or COO-alkyl group; m represents an integer of 0 to 3; n represents an integer of 0 to 4; and each X of the $(X)_m$ and each Y of the $(Y)n$ may be either identical or different; ⋯ represents a double bond or single bond; A is —$(CH_2)a$—(D)b—$(CH_2)c$—, wherein D is sulfur, NH, alkyl-substituted N or $CH_2$, a and c are integers of 0 to 10 and b is 0 or 1, or —(CH=CH)d—CH=, wherein d is an integer of 0 to 2, and B does not exist when A represents —(CH=CH)d—CH=, B refers to a hydrogen atom, alkyl group, amino group, monoalkylamino group, dialkylamino group, acylamino group, alkoxy group, trialkylsiloxy group or acyloxy group, and each of $R^1$, $R^2$, $R^3$ and $R^4$ is the same or different and is a hydrogen atom, straight or branched alkyl group having 1 to 7 carbon atoms, or a pharmacologically allowed cation; with the proviso that when D is sulfur, X is not a hydroxyl group and both a and c are 0; and with the proviso that when D is —$CH_2$—, or when d is 0 or 1, X is not an alkyl group and m is 2 to 3.

2. The methanediphosphonic acid derivative set forth in claim 1 wherein the naphthyl group is a 1-naphthyl or 2-naphthyl group.

3. A methanediphosphonic acid derivative which is selected from the group consisting of tetraethyl 2-naphthylthiomethanediphosphonate, 2-naphthylthiomethane, diphosphonic acid, tetraethyl 6-methoxy-2-naphthylthiomethanediphosphonate, 6-methoxy-2-naphthylthiomethanediphosphonic, acid, tetraethyl 6-hydroxy-2-naphthylthiomethanediphosphonate, 6-hydroxy-2-naphthylthiomethanediphosphonic, acid, tetraethyl 1-naphthylthiomethanediphosphonate, 1-naphthylthiomethanediphosphonic acid, tetraethyl 2-(3-methoxy-4-hydroxy-1-naphthyl)ethenylidene-1,1-diphosphonate, 2-(3-methoxy-4-hydroxy-1-naphthyl)ethenylidene-1,1-diphosphonic acid, tetraethyl 2-(3-methoxy-4-hydroxy-1-naphthyl)ethane-1,1-diphosphonate, 2-(3-methoxy-4-hydroxy-1-naphthyl)ethane-1,1-diphosphonic acid, tetraethyl 2-(3-methylthio-4-hydroxy-1-naphthyl) ethenylidene-1,1-diphosphonate, tetraethyl 2-(3-methylthio-4-hydroxy-1-naphthyl)ethane-1,1-diphosphonate, and 2-(3-methylthio-4-hydroxy-1-naphthyl)ethane-1,1-diphosphonic acid.

4. The methanediphosphonic acid derivative set forth in claim 1, which is 2-naphthylthiomethane diphosphonic acid.

5. The methanediphosphonic acid derivative set forth in claim 3, which is 6-methoxy-2-naphthylthiomethanediphosphonic acid.

6. The methanediphosphonic acid derivative set forth in claim 3, which is 6-hydroxy-2-naphthylthiomethanediphosphonic acid.

7. A pharmaceutical composition comprising a methane diphosphonic acid derivative set forth in claim 1 or 2, and a pharmaceutical acceptable carrier.

8. A method for the inhibition of inflammation comprising administering to a subject a methane diphosphonic acid derivative set forth in claim 1 or 2.

9. A method for the treatment of rheumatism comprising administering to a subject a methane disphosphonic acid derivative set forth in claim 1 or 2.

10. A method for the treatment of bone metabolic diseases comprising administering to a subject a methane diphosphonic acid derivative set forth in claim 1 or 2.

11. A method for the inhibition of interleukin-1 production or interleukin-1 induced cellular response comprising administering to a subject a methane diphosphonic acid derivative set forth in claim 1 or 2.

12. A method for the inhibition of active oxygen production in neutrophels comprising administering to a subject a methane diphosphonic acid derivative set forth in claim 1 or 2.

13. A method for the inhibition of bone resorption comprising administering to a subject a methane diphosphonic acid derivative set forth in claim 1 or 2.

* * * * *

UNITED STATES PATENT AND TRADEMARK OFFICE
CERTIFICATE OF CORRECTION

PATENT NO. : 5,618,804

DATED : April 8, 1997

INVENTOR(S): Norio KAWABE, Hiromi UCHIRO, Teruo NAKADATE, Masahiko TANANASHI, and Yuriko FUNABA It is certified that error appears in the above-identified patent and that said Letters Patent is hereby corrected as shown below:

Column 16, Line 38, change "articularheumatism" to --articularrheumatism--;
Column 16, Line 45, change "bind" to --hind--;
Column 19, Line 42, change "S-labelled" to --$^{35}$S-labelled--; and
Column 20, Line 55, change "$10^9$M" to --$10^{-7}$M--.

Signed and Sealed this

Twenty-ninth Day of May, 2001

Attest:

NICHOLAS P. GODICI

*Attesting Officer*   *Acting Director of the United States Patent and Trademark Office*